(12) United States Patent
Han

(10) Patent No.: US 11,468,573 B2
(45) Date of Patent: Oct. 11, 2022

(54) METHOD AND SYSTEM FOR ENHANCED VISUALIZATION OF COLOR FLOW ULTRASOUND

(71) Applicant: General Electric Company, Schenectady, NY (US)

(72) Inventor: Jihye Han, Seongnam-si (KR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 950 days.

(21) Appl. No.: 16/220,287

(22) Filed: Dec. 14, 2018

(65) Prior Publication Data
US 2020/0193613 A1 Jun. 18, 2020

(51) Int. Cl.
| | | |
|---|---|---|
| A61B 8/00 | (2006.01) | |
| G06T 7/20 | (2017.01) | |
| G01S 7/52 | (2006.01) | |
| G01S 15/58 | (2006.01) | |
| A61B 8/08 | (2006.01) | |
| A61B 8/06 | (2006.01) | |

(52) U.S. Cl.
CPC .......... G06T 7/20 (2013.01); A61B 8/06 (2013.01); A61B 8/52 (2013.01); G01S 7/52026 (2013.01); G01S 15/586 (2013.01); G06T 2207/10132 (2013.01); G06T 2207/30104 (2013.01)

(58) Field of Classification Search
IPC ................................................ A61B 8/06,8/52
See application file for complete search history.

(56) References Cited

U.S. PATENT DOCUMENTS

| | | | |
|---|---|---|---|
| 2003/0236460 A1* | 12/2003 | Ma ..................... | G01S 7/52077 600/441 |
| 2012/0130249 A1* | 5/2012 | Lee ..................... | A61B 8/06 600/454 |
| 2013/0241929 A1* | 9/2013 | Massarwa ............ | A61B 5/7425 345/421 |

* cited by examiner

*Primary Examiner* — Joel F Brutus
(74) *Attorney, Agent, or Firm* — McAndrews, Held & Malloy, Ltd.; Jacob Groethe; David Bates

(57) ABSTRACT

A system and method for enhancing visualization of color flow ultrasound is provided. The method includes generating estimated parameter values from filtered ultrasound image data. The method includes applying filter thresholds to the estimated parameter values, wherein the filter thresholds comprise first and second high power rejection thresholds and first and second low power and low velocity rejection thresholds. The method includes applying a transparency map to the estimated parameter values between the first and second high power rejection thresholds and between the first and second low power and low velocity rejection thresholds. The method includes generating a color flow image based at least in part on the estimated parameter values. The method includes presenting the color flow image at a display system.

20 Claims, 4 Drawing Sheets

-- PRIOR ART --

METHOD AND SYSTEM FOR ENHANCED VISUALIZATION OF COLOR FLOW ULTRASOUND

FIELD

Certain embodiments relate to ultrasound imaging. More specifically, certain embodiments relate to a method and system for providing enhanced visualization of color flow ultrasound. In various embodiments, two high power rejection thresholds and two low power and low velocity rejection thresholds are provided. The color flow data between the two high power rejection thresholds and between the two low power and low velocity rejection thresholds may be mapped to transparency values to provide additional information and increase the signal-to-noise (SNR) ratio by presenting the color flow data between the thresholds with a degree of transparency.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Known methods of performing diagnostic ultrasound imaging include B- and M-modes (used to image internal, physical structure), Doppler mode, and color flow mode, among other things. The color flow mode is primarily used to image flow characteristics, such as flow characteristics in blood vessels. For example, ultrasound color flow mode may be applied to detect the velocity of blood flow toward/away from an ultrasound transducer. Ultrasound color flow mode utilizes similar techniques used in Doppler mode. Whereas the Doppler mode displays velocity versus time for a single selected sample volume, ultrasound color flow mode displays hundreds of adjacent sample volumes simultaneously. The adjacent sample volumes are overlaid on a B-mode image and color-coded to represent each sample volume's velocity.

Using Doppler mode effects to measure blood flow in the heart and vessels is known. The amplitude of the reflected waves may be employed to produce black and white images of the tissues, while the frequency shift of backscattered waves may be used to measure the velocity of the backscatterer from tissue or blood. The change or shift in backscattered frequency increases when blood flows toward the ultrasound transducer and decreases when blood flows away from the ultrasound transducer. Color flow images may be produced by superimposing a color image of the velocity of the moving material, blood for example, over the black and white anatomical image. The measured velocity of flow at each pixel determines its color.

One limitation associated with taking Doppler effect measurements of reflected ultrasound waves from blood is that the received echo signal typically contains a large component produced by stationary or slow moving tissues (alternatively referred to as "clutter" and "color flash artifacts" respectively), whereas the blood reflects ultrasound waves very weakly. The stationary tissues in the blood do not produce any frequency shift in the reflected waves. Therefore, these components may be easily filtered out (alternatively referred to as "clutter suppression") without affecting the flow measurement. However, the reflections produced by moving tissue due to cardiac or respiratory motion are frequency shifted and may completely overwhelm signals from the slowly flowing blood.

In standard color flow processing, a high pass filter (alternatively referred to as a "wall filter") may be applied to the data before a color flow estimate is made. The wall filter may be configured to remove clutter noise. Additional filtering may be performed in connection with the color flow estimates. For example, FIG. 1 illustrates an exemplary flow classification graph as known in the art. Referring to FIG. 1, a signal processor of the ultrasound system may be configured to filter signal components above a high power rejection threshold and below a low power and low velocity rejection threshold. The filter thresholds are applied to filter out noise, such as tissue, patient, and probe movements when attempting to view blood flow. However, if the high power rejection threshold is set too low or the low power and low velocity rejection threshold is set too high, there is a risk of eliminating signal components associated with blood flow, such as micro blood flow, for example. Conversely, if the high power rejection threshold is set too high or the low power and low velocity rejection threshold is set too low, unwanted noise may be displayed.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for enhancing visualization of color flow ultrasound, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
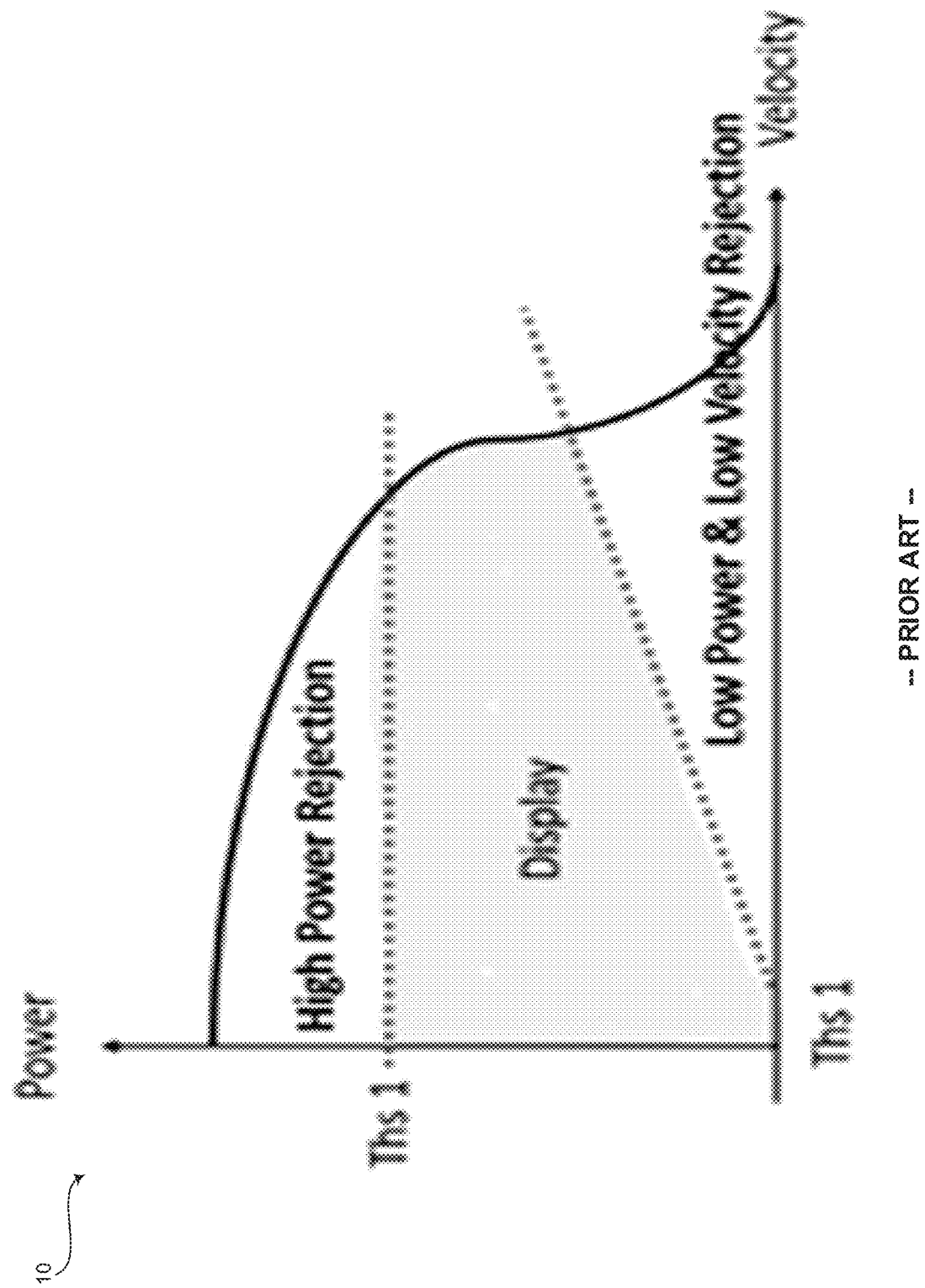
FIG. 1 illustrates an exemplary flow classification graph as known in the art

Certain embodiments may be found in a method and system for providing enhanced visualization of color flow ultrasound. Various embodiments have the technical effect of providing the enhanced visualization by applying two high power rejection thresholds and two low power and low velocity rejection thresholds. The color flow data between the two high power rejection thresholds and between the two low power and low velocity rejection thresholds may be mapped to transparency values to provide additional information and increase the signal-to-noise (SNR) ratio by presenting the color flow data between the thresholds with a degree of transparency.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 2.

Figure 2:
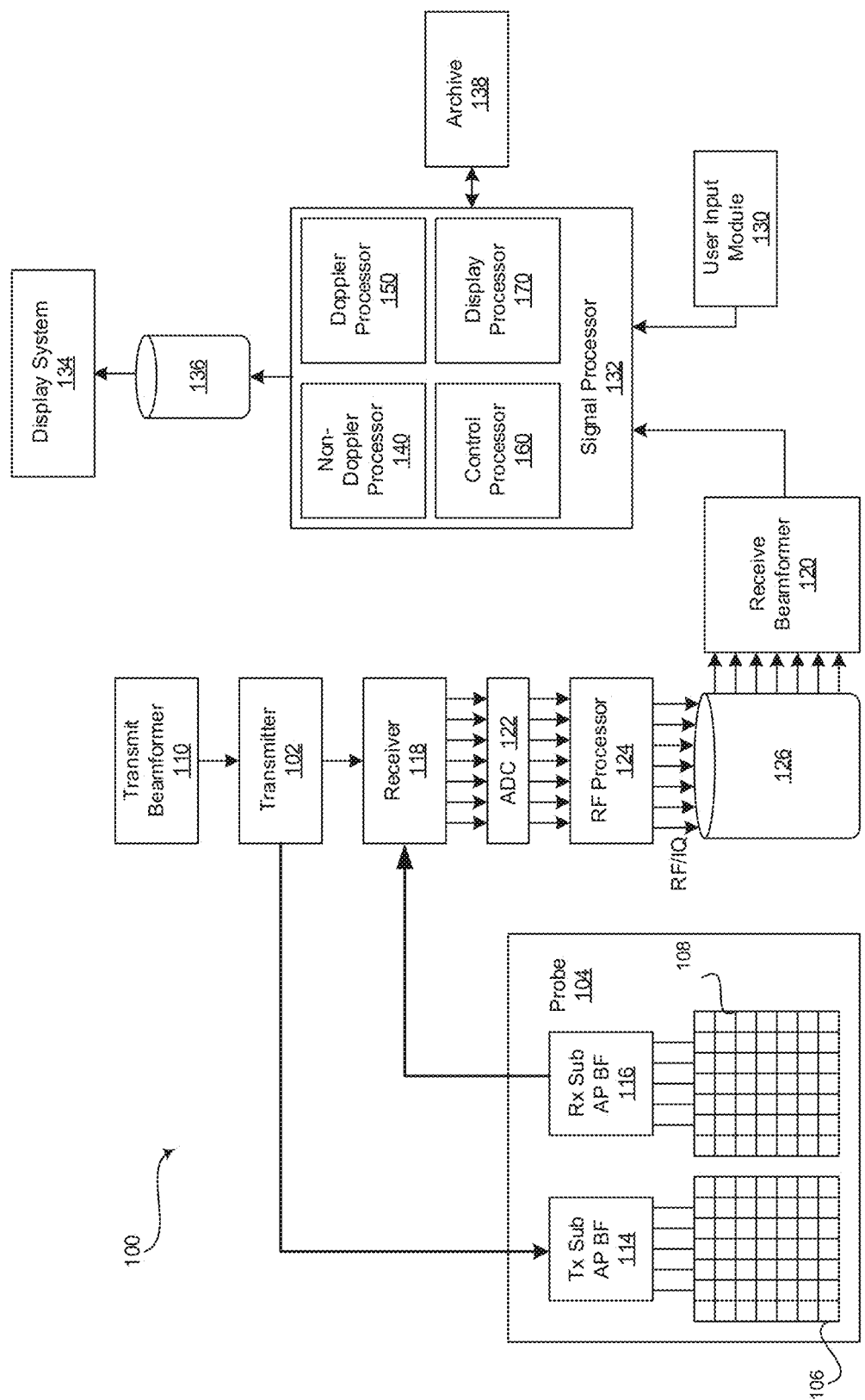
FIG. 2 is a block diagram of an exemplary ultrasound system that is operable to enhance visualization of color flow ultrasound, in accordance with various embodiments.

FIG. 2 is a block diagram of an exemplary ultrasound system that is operable to enhance visualization of color flow ultrasound, in accordance with various embodiments. Referring to FIG. 2, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input module 130 may be utilized to input patient data, scan parameters, settings, select protocols and/or templates, select an examination type, select filtering thresholds, and the like. In an exemplary embodiment, the user input module 130 may be operable to configure, manage and/or control operation of one or more components and/or modules in the ultrasound system 100. In this regard, the user input module 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, the display system 134, and/or the archive 138. The user input module 130 may include button(s), rotary encoder(s), a touchscreen, motion tracking, voice recognition, a mousing device, keyboard, camera and/or any other device capable of receiving a user directive. In certain embodiments, one or more of the user input modules 130 may be integrated into other components, such as the display system 134, for example. As an example, user input module 130 may include a touchscreen display.

In various embodiments, an examination type and/or filtering thresholds may be selected at the onset of an imaging procedure in response to a directive received via the user input module 130. For example, an ultrasound operator may identify a mitral regurgitation examination via the user input module 130 so that the signal processor 132 may apply a first set of high power rejection thresholds and a first set of low power and low velocity rejection thresholds while performing a color-flow mapping imaging procedure. The first set of high power rejection thresholds and the first set of low power and low velocity rejection thresholds may be optimized for the mitral regurgitation examination. The first set of high power rejection thresholds and the first set of low power and low velocity rejection thresholds may be stored in archive 138 and/or any suitable data storage medium and retrieved by the signal processor 132 in response to the examination-type selection. As another example, the ultrasound operator may select a first set of high power rejection threshold levels and a first set of low power and low velocity rejection threshold levels via the user input module 130 for application by the signal processor 132. Each of the selectable high power rejection levels may be associated with different high power rejection thresholds. Each of the selectable low power and low velocity levels may be associated with different low power and low velocity rejection thresholds. The different combinations of high power rejection thresholds and low power and low velocity rejection thresholds may each be associated with a transparency map. The transparency map may be stored in archive 138 and/or any suitable data storage medium and retrieved by the signal processor 132 in response to the examination-type selection or threshold level selections for application during Doppler processing to the color image data.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform Doppler processing, non-Doppler processing, display processing, and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a non-Doppler processor 140, a Doppler processor 150, a control processor 160, and a display processor 170 and may be capable of receiving input information from a user input module 130 and/or archive 138, generating an output displayable by a display system 134, and manipulating the output in response to input information from a user input module 130, among other things. The signal processor 132, non-Doppler processor 140, Doppler processor 150, control processor 160, and display processor 170 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a non-Doppler processor 140 that comprises suitable logic, circuitry, interfaces and/or code that may be operable to provide amplitude detection functions and data compression functions used for imaging modes such as B-mode, M-mode, harmonic imaging, and the like. For example, the non-Doppler processor 140 may receive digital signal data from the receive beamformer 120 and process the digital signal data to form the envelope of the beamsummed signal. The envelope of the signal may undergo additional processing, such as logarithmic compression, to form display data that is output to the display processor 170 and/or the control processor 160.

The signal processor 132 may include a Doppler processor 150 that comprises suitable logic, circuitry, interfaces and/or code that may be operable to provide clutter filtering functions and movement parameter estimation functions used for imaging modes such as color flow (CF) imaging, tissue velocity imaging (TVI), strain rate imaging (SRI), and the like. For example, the Doppler processor 150 may be configured to receive digital signal data from the receive beamformer 120 and perform wall filtering, vector interpolation, power recompression, and velocity calculation. In various embodiments, the Doppler processor 150 may apply filter thresholds and a transparency map to estimated parameter values to generate Doppler display data that is provided to the display processor 170 and/or the control processor 160. In certain embodiments, the filtering may be applied in connection with the velocity calculation performed by the Doppler processor 150. The filter thresholds may include first and second high power rejection thresholds and first and second low power and low velocity rejection thresholds. The signal values between the lowest high power rejection threshold and the highest low power and low velocity rejection threshold may be fully displayed as opaque color values. The signal values above the highest power rejection threshold and below the lowest low power and low velocity rejection threshold are fully filtered out and not displayed. The transparency map may be applied to values between the first and second high power rejection thresholds and between the first and second low power and low velocity rejection thresholds to provide additional information and increase the signal-to-noise (SNR) ratio by presenting the color flow data between the thresholds with a degree of transparency.

In various embodiments, the transparency may be applied non-linearly between the thresholds of both the high power rejection thresholds and the low power and low velocity rejection thresholds. For example, the transparency may be determined by calculating the distribution between the first and second thresholds for each of the high power rejection thresholds and the low power and low velocity rejection thresholds. In various embodiments, between the first and second thresholds for each of the high power rejection thresholds and the low power and low velocity rejection thresholds, up to 75% of the values close to the first threshold may be less transparent and clearly visible while the remaining 25% may be more transparent and less visible.

In certain embodiments, the thresholds and transparency map may be selected based on an associated examination-type, user threshold level selections, or any suitable selection criteria. For example, the Doppler processor 150 may be configured to retrieve a set of thresholds and transparency map from archive 138 or any suitable data storage medium in response to a user directive via the user input module 130 to select a particular imaging examination. The thresholds and transparency map may be applied by the Doppler processor 150 to the ultrasound data acquired according to the selected imaging examination.

Figure 3:
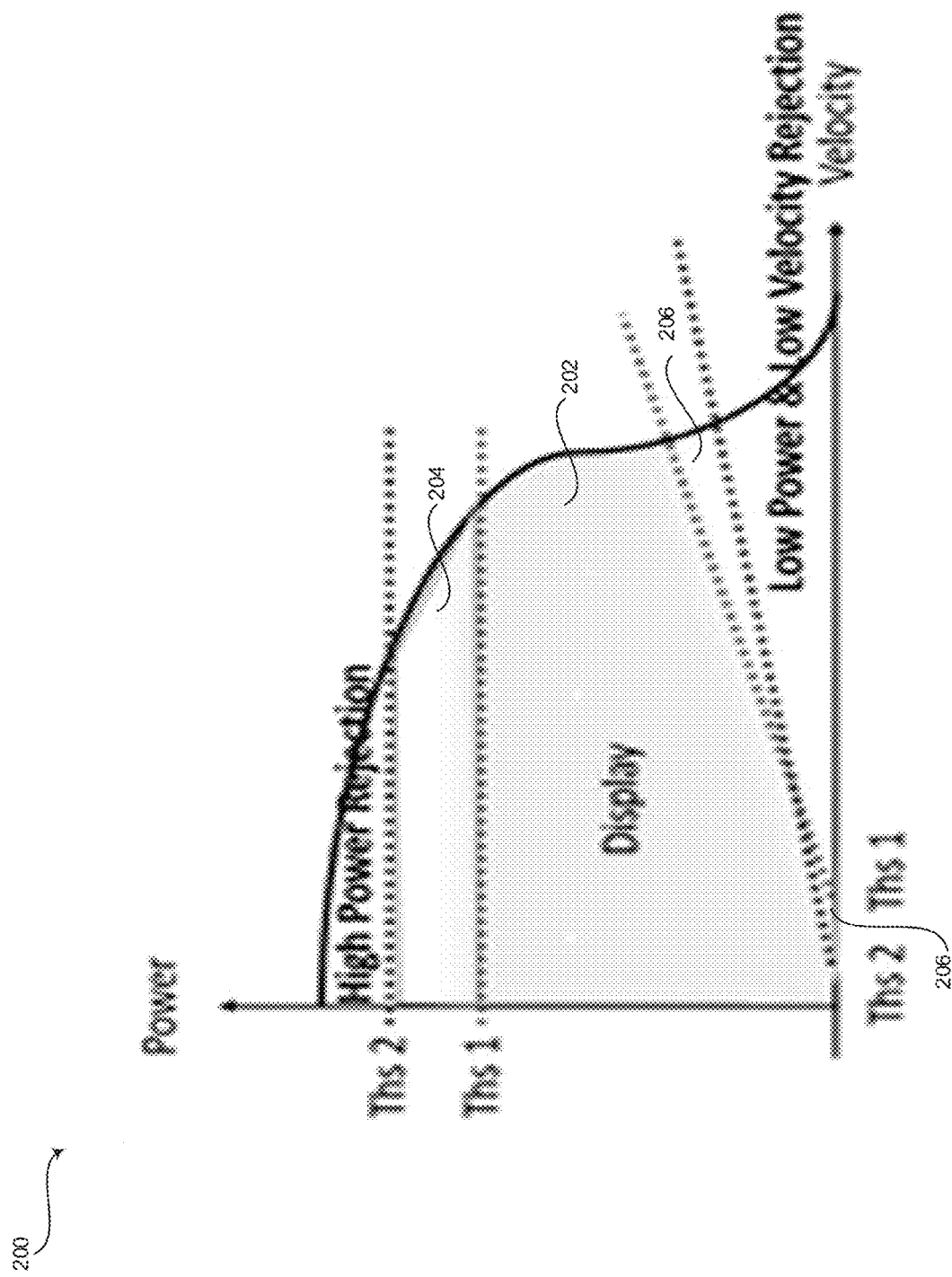
FIG. 3 is an exemplary flow classification graph, in accordance with various embodiments.

FIG. 3 is an exemplary flow classification graph 200, in accordance with various embodiments. Referring to FIG. 3, the flow classification graph 200 includes first (Ths 1) and second (Ths 2) high power rejection thresholds and first (Ths 1) and second (Ths 2) low power and low velocity rejection thresholds. The signal values above the second high power rejection threshold (Ths 2) and below portions of the first (Ths 1) and second (Ths 2) low power and low velocity rejection thresholds are filtered out and/or not displayed (i.e., fully transparent). The signal values 202 below the first (Ths 1) high power rejection threshold and above portions of the first (Ths 1) and second (Ths 2) low power and low rejection thresholds are fully displayed (i.e., opaque). The signal values 204 between the first high power rejection threshold (Ths 1) and the second high power rejection threshold (Ths 2) are mapped to transparency values each having a transparency level (i.e., partially transparent). The signal values 206 between the first (Ths 1) and second (Ths 2) low power and low velocity rejection thresholds are mapped to transparency values each having a transparency level (i.e., partially transparent). The level of transparency may be applied non-linearly to the signal values 204, 206 between the first (Ths 1) and second (Ths 2) thresholds of each of the high power rejection and low power and low velocity rejection thresholds.

Referring again to FIG. 2, the signal processor 132 may include a control processor 160 that comprises suitable logic, circuitry, interfaces and/or code that may be operable to execute the various data algorithms and functions for the various imaging and diagnostic modes. Digital data and commands may be communicated between the control processor 160 and other various parts of the ultrasound system 100. As an alternative, the functions performed by the control processor 160 may be performed by multiple processors, or may be integrated into processors 140, 150, or 170, or any combination thereof. As a further alternative, the functions of processors 140, 150, 160, and 170 may be integrated into a single PC backend.

The signal processor 132 may include a display processor 170 that comprises suitable logic, circuitry, interfaces and/or code that may be operable to process the non-Doppler display data from the non-Doppler processor 140 and/or control processor 160 and the Doppler display data from the Doppler processor 150 and/or control processor 160 to generate a color flow image for presentation at the display system 134. The display processor 170 may be configured to perform frame averaging on the Doppler display data, scan conversion, color mapping, and the like. The color flow images generated by the display processor 170 are presented at the display system 134 and may be stored in archive 138 or any suitable data storage medium.

The display system 134 may be any device capable of communicating visual information to a user. For example, a display system 134 may include a liquid crystal display, a light emitting diode display, and/or any suitable display or displays. The display system 134 can be operable to display information from the signal processor 132 and/or archive 138, such as color flow ultrasound images, and/or any suitable information. In various embodiments, the display system 134 is operable to present color flow images generated using Doppler display data processed based on first (Ths 1) and second (Ths 2) high power rejection thresholds, first (Ths 1) and second (Ths 2) low power and low velocity rejection thresholds, and transparency value mapping.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores medical image data, image acquisition parameters, non-Doppler processing parameters, Doppler processing parameters, display processing parameters, instructions for applying thresholds to filter color flow image data, and instructions for mapping transparency values to the color flow image data, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input module 130 may be integrated as a touchscreen display.

Figure 4:
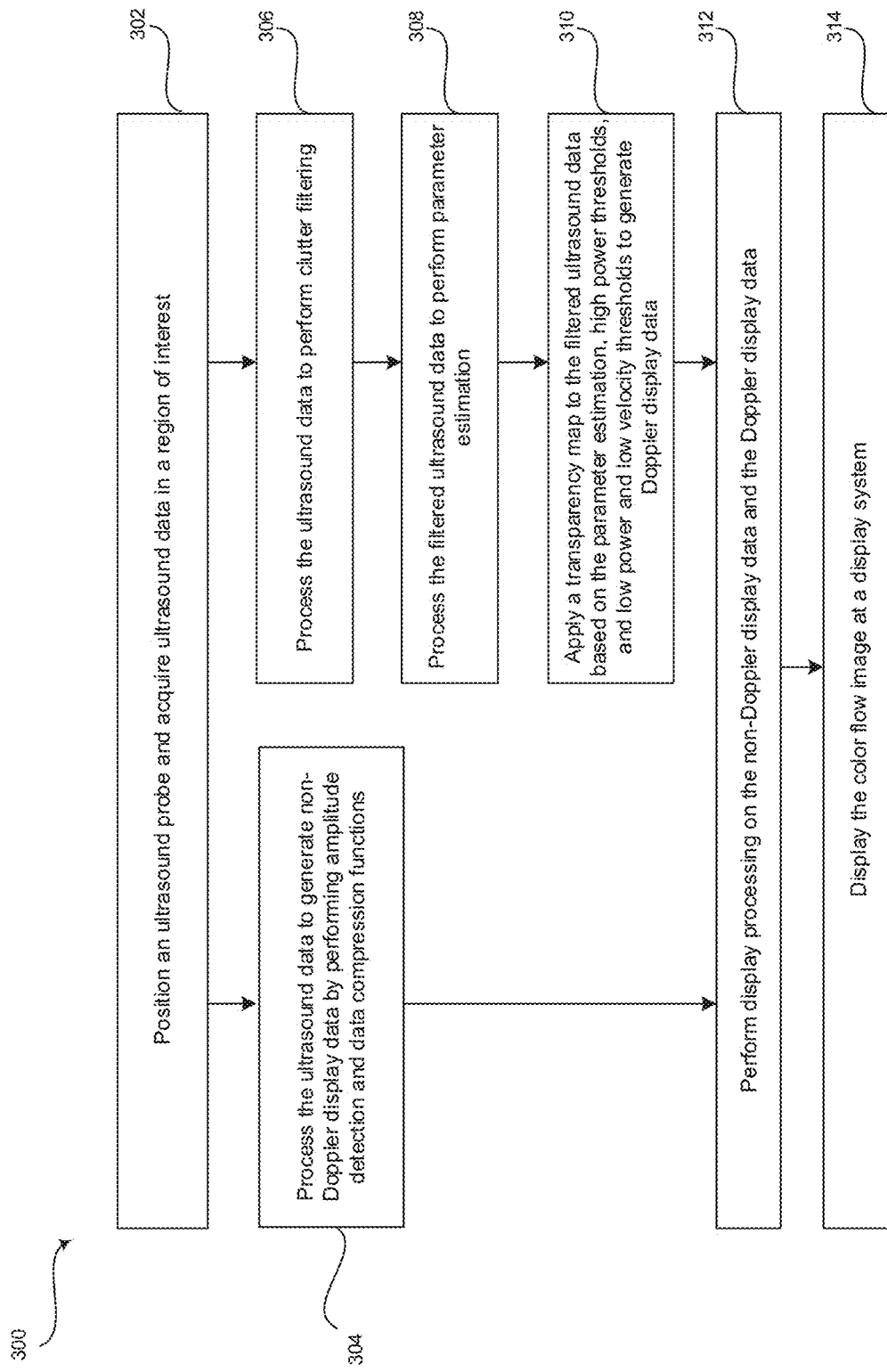
FIG. 4 is a flow chart illustrating exemplary steps that may be utilized for enhancing visualization of color flow ultrasound, in accordance with various embodiments.

FIG. 4 is a flow chart 300 illustrating exemplary steps 302-314 that may be utilized for enhancing visualization of color flow ultrasound, in accordance with various embodiments. Referring to FIG. 4, there is shown a flow chart 300 comprising exemplary steps 302 through 314. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 302, a probe 104 of an ultrasound system 100 may be positioned to acquire ultrasound data of a region of interest. For example, the ultrasound system 100 may acquire the ultrasound signals with an ultrasound probe 104 positioned over a region of interest, such as a blood vessel, a heart, and/or any suitable anatomical structures. In various embodiments, the probe 104 may be operable to acquire 2D ultrasound image data and Doppler signals.

At step 304, the signal processor 132 of the ultrasound system 100 may process the ultrasound data to generate non-Doppler display data by performing amplitude detection and data compression functions. For example, a non-Doppler processor 140 of the signal processor 132 may receive the 2D ultrasound image data acquired by probe 104 at step 302. The non-Doppler processor 140 may process the 2D ultrasound image data to form the envelope of the signal. The envelope of the signal may undergo additional processing, such as logarithmic compression, to form the non-Doppler display data.

At step 306, the signal processor 132 of the ultrasound system 100 may process the ultrasound data to perform clutter filtering. For example, a Doppler processor 150 of the signal processor 132 may receive the Doppler signals acquired by probe 104 at step 302. The Doppler processor 140 may apply a wall filter to perform clutter filtering of the received Doppler signals.

At step 308, the signal processor 132 of the ultrasound system 100 may process the filtered ultrasound data to perform parameter estimation. For example, the Doppler processor 150 of the signal processor 132 may perform vector interpolation, power recompression, and velocity calculation of the filtered ultrasound data to obtain estimated movement parameters.

At step 310, the signal processor 132 of the ultrasound system 100 may apply a transparency map to the filtered ultrasound data based on the parameter estimation, high power thresholds, and low power and low velocity thresholds to generate Doppler display data. For example, the Doppler processor 150 of the signal processor 132 may apply filter thresholds and a transparency map to estimated parameter values to generate Doppler display data. The filtering may be applied in connection with the velocity calculation performed by the Doppler processor 150. The filter thresholds may include first (Ths 1) and second (Ths 2) high power rejection thresholds and first (Ths 1) and second (Ths 2) low power and low velocity rejection thresholds. The signal values 202 between the lowest high power rejection threshold (Ths 1) and the highest low power and low velocity rejection threshold (Ths 2-Ths 1) may be fully displayed as opaque color values. The signal values above the highest power rejection threshold (Ths 2) and below the lowest low power and low velocity rejection threshold (Ths 1-Ths 2) are fully filtered out and not displayed. The transparency map may be applied to values 204, 206 between the first (Ths 1) and second (Ths 2) high power rejection thresholds and between the first (Ths 1) and second (Ths 2) low power and low velocity rejection thresholds to provide additional information and increase the signal-to-noise (SNR) ratio by presenting the color flow data between the thresholds with a degree of transparency. In various embodiments, the transparency may be applied non-linearly between the thresholds of both the high power rejection thresholds (Ths 1, Ths 2) and the low power and low velocity rejection thresholds (Ths 1, Ths 2). The thresholds and transparency map may be selected based on an associated examination-type, user threshold level selections, or any suitable selection criteria. The Doppler processor 150 may be configured to retrieve a set of thresholds and transparency map from archive 138 or any suitable data storage medium in response to the selecting imaging examination and/or threshold level selections.

At step 312, the signal processor 132 may perform display processing on the non-Doppler display data and the Doppler display data. For example, a display processor 170 of the signal processor 132 may process the non-Doppler display data from the non-Doppler processor 140 and the Doppler display data from the Doppler processor 150 to generate a color flow image. The display processor 170 may be configured to perform frame averaging on the Doppler display data, scan conversion, and color mapping, among other things.

At step 314, the signal processor 132 may display the color flow image at a display system 134. For example, the display processor 170 of the signal processor 132 may present the color flow images generated by the display processor 170 at step 312 at the display system 134. The ultrasound system 100 enhances visualization of the color flow images presented at the display system by providing additional information and increasing the signal-to-noise (SNR) ratio as a result of the color flow data between the first and second thresholds of each of the high power rejection thresholds and low power and low velocity rejection thresholds being presented with a degree of transparency.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing enhanced visualization of color flow ultrasound.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
   generating, by at least one processor, estimated parameter values from filtered ultrasound image data;
   applying, by the at least one processor, filter thresholds to the estimated parameter values, wherein the filter thresholds comprise a first high power rejection threshold, a second high power rejection threshold, a first low power and low velocity rejection threshold, and a second low power and low velocity threshold;
   applying, by the at least one processor, a transparency map to:
      the estimated parameter values between the first high power rejection threshold and the second high power rejection threshold, and
      the estimated parameter values between the first low power and low velocity rejection threshold and the second low power and low velocity rejection threshold;
   generating, by the at least one processor, a color flow image based at least in part on the estimated parameter values; and
   presenting, at a display system, the color flow image.

2. The method of claim 1, comprising performing, by the at least one processor, clutter filtering on ultrasound image data to generate the filtered ultrasound image data.

3. The method of claim 2, comprising acquiring, by an ultrasound probe, the ultrasound image data, wherein the ultrasound image data comprises Doppler signals.

4. The method of claim 1, wherein the estimated parameter values between a lowest of the first and second high power rejection thresholds and a highest of the first and second low power and low velocity rejection thresholds are fully displayed as opaque color values.

5. The method of claim 1, wherein the estimated parameter values above a highest of the first and second high power rejection thresholds and below a lowest of the first and second low power and low velocity rejection thresholds are not displayed.

6. The method of claim 1, wherein transparency values defined in the transparency map are non-linear.

7. The method of claim 1, comprising receiving, by the at least one processor, a selection of one of a plurality of examination-types via a user input module, wherein each of the plurality of examination-types is associated with different filter thresholds and transparency maps.

8. The method of claim 7, comprising retrieving, by the at least one processor, at least one of the filter thresholds and the transparency map from a data storage medium based on the received selection of the one of the plurality of examination-types.

9. A system comprising:
   at least one processor configured to:
      generate estimated parameter values from filtered ultrasound image data;
      apply filter thresholds to the estimated parameter values, wherein the filter thresholds comprise a first high power rejection threshold, a second high power rejection threshold, a first low power and low velocity rejection threshold, and a second low power and low velocity threshold;
      apply a transparency map to:
         the estimated parameter values between the first high power rejection threshold and the second high power rejection threshold, and
         the estimated parameter values between the first low power and low velocity rejection threshold and the second low power and low velocity rejection threshold; and
      generate a color flow image based at least in part on the estimated parameter values; and
   a display system configured to present the color flow image.

10. The system of claim 9, wherein the at least one processor is configured to perform clutter filtering on ultrasound image data to generate the filtered ultrasound image data.

11. The system of claim 10, comprising an ultrasound probe operable to acquire the ultrasound image data, wherein the ultrasound image data comprises Doppler signals.

12. The system of claim 9, wherein the estimated parameter values between a lowest of the first and second high power rejection thresholds and a highest of the first and second low power and low velocity rejection thresholds are fully displayed as opaque color values.

13. The system of claim 9, wherein the estimated parameter values above a highest of the first and second high power rejection thresholds and below a lowest of the first and second low power and low velocity rejection thresholds are not displayed.

14. The system of claim 9, wherein transparency values defined in the transparency map are non-linear.

15. The system of claim 9, comprising:
a user input module operable to provide a selection of one of a plurality of examination-types to the at least one processor, and
a data storage medium configured to store different filter thresholds and transparency maps associated with each of the plurality of examination-types,
wherein the at least one processor is configured to retrieve at least one of the filter thresholds and the transparency map from the data storage medium based on the selection of the one of the plurality of examination-types provided by the user input module.

16. A non-transitory computer readable medium having stored thereon, a computer program having at least one code section, the at least one code section being executable by a machine for causing the machine to perform steps comprising:
generating estimated parameter values from filtered ultrasound image data;
applying filter thresholds to the estimated parameter values, wherein the filter thresholds comprise a first high power rejection threshold, a second high power rejection threshold, a first low power and low velocity rejection threshold, and a second low power and low velocity threshold;
applying a transparency map to:
the estimated parameter values between the first high power rejection threshold and the second high power rejection threshold, and
the estimated parameter values between the first low power and low velocity rejection threshold and the second low power and low velocity rejection threshold;
generating a color flow image based at least in part on the estimated parameter values; and
presenting the color flow image at a display system.

17. The non-transitory computer readable medium of claim 16, comprising:
acquiring ultrasound image data, wherein the ultrasound image data comprises Doppler signals; and
performing clutter filtering on the ultrasound image data to generate the filtered ultrasound image data.

18. The non-transitory computer readable medium of claim 16, wherein:
the estimated parameter values between a lowest of the first and second high power rejection thresholds and a highest of the first and second low power and low velocity rejection thresholds are fully displayed as opaque color values; and
the estimated parameter values above a highest of the first and second high power rejection thresholds and below a lowest of the first and second low power and low velocity rejection thresholds are not displayed.

19. The non-transitory computer readable medium of claim 16, wherein transparency values defined in the transparency map are non-linear.

20. The non-transitory computer readable medium of claim 16, comprising:
receiving a selection of one of a plurality of examination-types, wherein each of the plurality of examination-types is associated with different filter thresholds and transparency maps; and
retrieving at least one of the filter thresholds and the transparency map from a data storage medium based on the received selection of the one of the plurality of examination-types.

* * * * *